United States Patent
Fung et al.

(10) Patent No.: US 7,186,875 B2
(45) Date of Patent: *Mar. 6, 2007

(54) CONVERSION OF OXYGENATES TO OLEFINS

(75) Inventors: Shun Chong Fung, Bridgewater, NJ (US); Doron Levin, Annandale, NJ (US); Jose Santiesteban, Baton Rouge, LA (US); Nicolas P. Coute, Houston, TX (US)

(73) Assignee: Exxon Mobil Chemical Patents Inc., Houston, TX (US)

( * ) Notice: Subject to any disclaimer, the term of this patent is extended or adjusted under 35 U.S.C. 154(b) by 192 days.

This patent is subject to a terminal disclaimer.

(21) Appl. No.: 10/909,012

(22) Filed: Jul. 30, 2004

(65) Prior Publication Data

US 2006/0025645 A1 Feb. 2, 2006

(51) Int. Cl.
*C07C 1/00* (2006.01)
(52) U.S. Cl. .................. 585/640; 585/638; 585/639
(58) Field of Classification Search ......... 585/638–640
See application file for complete search history.

(56) References Cited

U.S. PATENT DOCUMENTS

| | | | | |
|---|---|---|---|---|
| 4,062,905 A | 12/1977 | Chang et al. | ............... | 260/682 |
| 4,079,095 A | 3/1978 | Givens et al. | ............... | 260/682 |
| 4,310,440 A | 1/1982 | Wilson et al. | ............... | 252/435 |
| 4,440,871 A | 4/1984 | Lok et al. | .................... | 502/214 |
| 4,499,327 A | 2/1985 | Kaiser | ........................ | 585/640 |
| 4,677,242 A | 6/1987 | Kaiser | ......................... | 585/638 |
| 4,677,243 A | 6/1987 | Kaiser | ......................... | 585/638 |
| 4,789,528 A | 12/1988 | Owen et al. | ................. | 422/190 |
| 4,873,390 A | 10/1989 | Lewis et al. | ................. | 585/638 |
| 5,095,163 A | 3/1992 | Barger | ......................... | 585/640 |
| 5,367,100 A | 11/1994 | Gongwei et al. | ........... | 585/640 |
| 5,714,662 A | 2/1998 | Vora et al. | .................... | 585/640 |
| 6,023,005 A | 2/2000 | Lattner et al. | .............. | 585/639 |
| 6,166,282 A | 12/2000 | Miller | ......................... | 585/638 |
| 6,187,983 B1 * | 2/2001 | Sun | .............................. | 585/638 |
| 6,995,111 B2 * | 2/2006 | Levin et al. | ................. | 502/214 |
| 2003/0176752 A1 | 9/2003 | Levin et al. | ................. | 585/640 |
| 2003/0176753 A1 | 9/2003 | Levin et al. | ................. | 585/640 |

FOREIGN PATENT DOCUMENTS

WO    WO 01/64340 A1 * 9/2001

OTHER PUBLICATIONS

Kang et al., "Effects of Decrease in Number of Acid Sites Located on the External Surface of Ni-SAPO-34 Crystalline Catalyst by the Mechanochemical Method", Catalysis Letters, vol. 53, pp. 171-176 (1998).*

* cited by examiner

*Primary Examiner*—In Suk Bullock

(57) ABSTRACT

A process is described for converting an oxygenate-containing feedstock into one or more olefins in a reactor system including a plurality of fixed bed reactors each containing a catalyst composition comprising a molecular sieve and at least one metal oxide having an uptake of carbon dioxide at 100° C. of at least 0.03 mg/m² of the metal oxide. Each reactor is sequentially rotated between at least one operating mode, wherein the catalyst composition in the reactor is contacted with the oxygenate-containing feedstock, and a regeneration mode, wherein the catalyst composition in the reactor is contacted with a regeneration medium.

23 Claims, 1 Drawing Sheet

CONVERSION OF OXYGENATES TO OLEFINS

FIELD OF INVENTION

This invention relates to a method for catalytically converting a feed including an oxygenated hydrocarbon to a light olefin product in a fixed bed reactor system.

BACKGROUND

Light olefins, such as ethylene, propylene, butylenes and mixtures thereof, serve as feeds for the production of numerous important chemicals and polymers. Typically, $C_2$–$C_4$ light olefins are produced by cracking petroleum refinery streams, such as $C_3$+ paraffinic feeds. In view of limited supply of competitive petroleum feeds, production of low cost light olefins from petroleum feeds are subject to waning supplies. Efforts to develop light olefin production technologies based on alternative feeds have therefore increased.

An important type of alternative feed for the production of light olefins is oxygenates, such as $C_1$–$C_4$ alkanols, especially methanol and ethanol; $C_2$–$C_4$ dialkyl ethers, especially dimethyl ether (DME), methyl ethyl ether and diethyl ether; dimethyl carbonate and methyl formate, and mixtures thereof. Many of these oxygenates may be produced from alternative sources by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as economical, non-petroleum sources for light olefin production.

The preferred process for converting an oxygenate feedstock, such as methanol, into one or more olefin(s), primarily ethylene and/or propylene, involves contacting the feedstock with a molecular sieve catalyst composition. Molecular sieves are porous solids having pores of different sizes, such as zeolites or zeolite-type molecular sieves, carbons and oxides. The most commercially useful molecular sieves for the petroleum and petrochemical industries are zeolites, for example aluminosilicate molecular sieves. Zeolites in general have a one-, two- or three-dimensional crystalline pore structure having uniformly sized pores of molecular dimensions that selectively adsorb molecules that can enter the pores, and exclude those molecules that are too large.

There are many different types of molecular sieve well known to convert a feedstock, especially an oxygenate containing feedstock, into one or more olefin(s). For example, U.S. Pat. No. 5,367,100 describes the use of the zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; U.S. Pat. No. 4,079,095 describes the use of ZSM-34 to convert methanol to hydrocarbon products such as ethylene and propylene; and U.S. Pat. No. 4,310,440 describes producing light olefin(s) from an alcohol using a crystalline aluminophosphate, often designated $AlPO_4$.

Some of the most useful molecular sieves for converting methanol to olefin(s) are silicoaluminophosphate molecular sieves. Silicoaluminophosphate (SAPO) molecular sieves contain a three-dimensional microporous crystalline framework structure of $[SiO_4]$, $[AlO_4]$ and $[PO_4]$ corner sharing tetrahedral units. SAPO synthesis is described in U.S. Pat. No. 4,440,871, which is herein fully incorporated by reference. SAPO molecular sieves are generally synthesized by the hydrothermal crystallization of a reaction mixture of silicon-, aluminum- and phosphorus-sources and at least one templating agent. Synthesis of a SAPO molecular sieve, its formulation into a SAPO catalyst, and its use in converting a hydrocarbon feedstock into olefin(s), particularly where the feedstock is methanol, are disclosed in U.S. Pat. Nos. 4,499,327, 4,677,242, 4,677,243, 4,873,390, 5,095,163, 5,714,662 and 6,166,282, all of which are herein fully incorporated by reference.

Conversion of oxygenates to olefins generates and deposits carbonaceous material (coke) on the molecular sieve catalysts used to catalyze the conversion process. Over-accumulation of these carbonaceous deposits will inhibit the catalyst's ability to promote the reaction. In order to avoid unwanted build-up of coke on the molecular sieve catalyst, the oxygenate to olefin process generally incorporates a second step comprising catalyst regeneration. During regeneration, the coke is removed from the catalyst, typically by combustion with oxygen, which at least partially restores the catalytic activity of the catalyst. The regenerated catalyst then may be reused to catalyze the conversion of oxygenates to olefins.

For example, SAPO-34 is known to be a selective molecular sieve catalyst in the conversion of methanol to ethylene and propylene. However, its excellent selectivity to ethylene and propylene (maximum selectivity about 40–43 wt % each) requires the formation of a carbon pool as carbonaceous material is being deposited on the catalyst. With fresh catalyst, ethylene and propylene selectivities are about 20–24 wt % and about 32–36 wt % respectively rising to their maximum values with time as more carbonaceous material is being deposited. However, catalyst activity drops off rapidly when the carbonaceous material is greater than about 10 wt % (based on SAPO-34 molecular sieve content). Fixed bed operation is not practical since catalyst life under a reasonable space velocity (at least 3 w/w/hr) is less than 2.5 hours. For this reason most current proposals for converting oxygenates to olefins employ a fluidized bed reactor in which the catalyst is continuously circulated between a riser reactor and a regenerator.

It would, however, be desirable to provide an improved molecular sieve catalyst composition and process which would enable a fixed bed reactor system to be employed in an economically viable manner in the conversion of oxygenates, such as methanol, to olefins.

U.S. Pat. No. 4,873,390 to Lewis et al., incorporated herein by reference, teaches conversion of a feedstock, e.g., alcohols, to a product containing light olefins over a silicoaluminophosphate catalyst having pores with a diameter of less than 5 Angstroms, wherein a carbonaceous deposit material is formed on the catalyst. The catalyst is treated to form a partially regenerated catalyst having from 2 to 30 wt. % of the carbonaceous deposit material. The catalyst is preferably in a fluidized state and is continuously transported between the reaction zone and the regeneration zone.

U.S. Pat. No. 6,023,005 to Lattner et al., incorporated herein by reference, discloses a method of producing ethylene and propylene by catalytic conversion of oxygenate in a fluidized bed reaction process which utilizes catalyst regeneration. The process maintains a portion of desired carbonaceous deposits on the catalyst by removing only a portion of the total reaction volume of coked molecular sieve catalyst and regenerating only that portion of catalyst, which is then mixed back with the unregenerated remainder of catalyst. The resulting catalyst mixture contains 2–30 wt % carbonaceous deposits.

In our co-pending U.S. Patent Publication No. 2003/0176752 published Sep. 18, 2003, incorporated herein by reference, there is described a catalyst composition that exhibits enhanced lifetime when used in the conversion of oxygenates to olefins and which comprises a molecular sieve and at least one metal oxide having an uptake of carbon dioxide at 100° C. of at least 0.03 mg/m$^2$ of the metal oxide. The metal oxide is selected from an oxide of Group 4 of the Periodic Table of Elements, either alone or in combination with an oxide selected from Group 2 of the Periodic Table of Elements and/or an oxide selected from Group 3 of the Periodic Table of Elements, including the Lanthanide series of elements and the Actinide series of elements.

In our co-pending U.S. Patent Publication No. 2003/0176753 published Sep. 18, 2003, incorporated herein by reference, there is described a catalyst composition that exhibits enhanced lifetime when used in the conversion of oxygenates to olefins and which comprises a molecular sieve and at least one metal oxide having an uptake of carbon dioxide at 100° C. of at least 0.03 mg/m$^2$ of the metal oxide. The metal oxide is selected from an oxide of a metal from Group 3 of the Periodic Table of Elements, the Lanthanide series of elements and the Actinide series of elements.

U.S. Pat. No. 4,789,528 to Owen et al., incorporated herein by reference, teaches a multi-reactor system for the conversion of light olefins to gasoline and/or distillate in which at least three reactors are sequentially rotated between a regeneration mode and at least two serially connected reaction modes respectively. In the reaction modes, the reactor having relatively less fresh catalyst receives feed from a feed source first and the reactor having the fresher catalyst receives the feed last.

SUMMARY

The present invention relates to a process for converting an oxygenate-containing feedstock into one or more olefins in a reactor system including a plurality of fixed bed reactors each containing a catalyst composition comprising a molecular sieve and at least one metal oxide having an uptake of carbon dioxide at 100° C. of at least 0.03 mg/m$^2$ of the metal oxide, wherein each reactor is sequentially rotated between at least one operating mode, wherein the catalyst composition in the reactor is contacted with the oxygenate-containing feedstock, and a regeneration mode, wherein the catalyst composition in the reactor is contacted with a regeneration medium.

In one embodiment, the reactor system comprises at least three of said fixed bed reactors and each reactor is sequentially rotated from said regeneration mode to a first operating mode, then to at least a second operating mode and then back to said regeneration mode, wherein reactors in said first and second operating modes are connected in series such that the oxygenate-containing feedstock contacts the catalyst composition in a reactor in the second operating mode before contacting the catalyst composition in a reactor in the first operating mode.

Conveniently, the metal of said at least one metal oxide is selected from Group 2, Group 3 (including the Lanthanide and Actinide series metals) and Group 4 of the Periodic Table of Elements using the IUPAC format described in the *CRC Handbook of Chemistry and Physics,* 78th Edition, CRC Press, Boca Raton, Fla. (1997). For example, the metal oxide may be selected from zirconium oxide, hafnium oxide, magnesium oxide, calcium oxide, barium oxide, lanthanum oxide, yttrium oxide, scandium oxide, cerium oxide, and mixtures thereof.

Conveniently, the catalyst composition also includes at least one of a binder and a matrix material different from the metal oxide.

In one embodiment, the molecular sieve comprises a framework including at least two tetrahedral units selected from [SiO$_4$], [AlO$_4$] and [PO$_4$] units, such as a silicoaluminophosphate.

In a preferred embodiment, the present invention employs a molecular sieve which has a pore diameter of less than 5.0 Angstroms, e.g., a molecular sieve having a framework-type selected from AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. For example, the molecular sieve may be selected from ALPO-18, ALPO-34, SAPO-17, SAPO-18, and SAPO-34.

DETAILED DESCRIPTION OF THE EMBODIMENTS

Introduction

Figure 1:
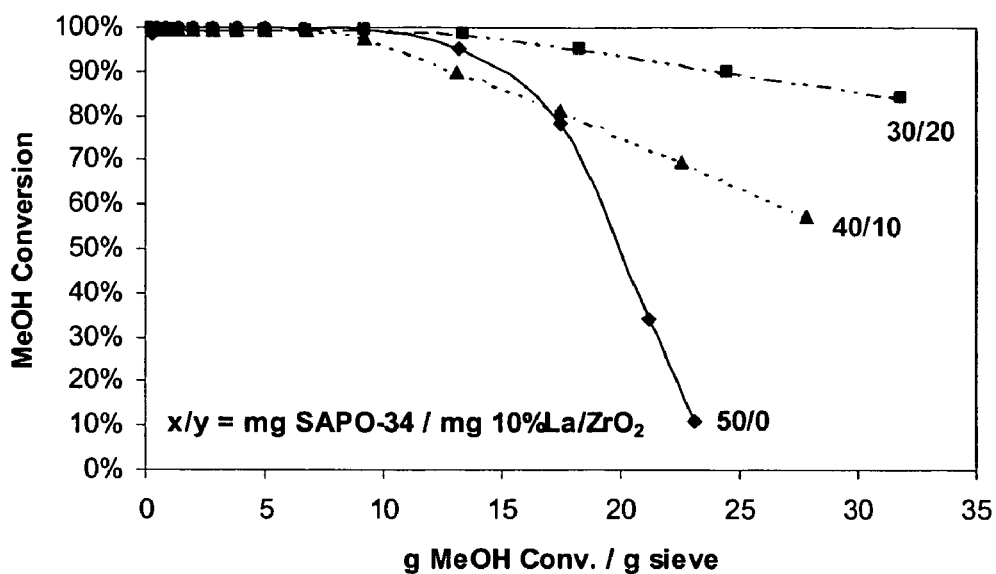
FIG. 1 is a graph illustrating the decrease in methanol conversion with time on stream for a catalyst composition comprising SAPO-34 molecular sieve and varying amounts of La/ZrO$_2$.

The present invention provides a process for converting an oxygenate-containing feedstock into one or more olefins in a reactor system which includes a plurality of fixed bed reactors. Each of the fixed bed reactors contains a catalyst composition comprising a molecular sieve and at least one metal oxide having an uptake of carbon dioxide at 100° C. of at least 0.03 mg/m$^2$ of the metal oxide. In particular, it has been found that combining a molecular sieve with such a metal oxide results in a marked increase in the lifetime of the catalyst composition when used in the conversion of oxygenates into olefins. As a result, it has for the first time become feasible to conduct the conversion process in a multi-reactor system wherein each reactor is sequentially rotated between at least one operating mode, wherein the catalyst composition in the reactor is contacted with the oxygenate-containing feedstock, and a regeneration mode, wherein the catalyst composition in the reactor is contacted with a regeneration medium.

In one practical embodiment, the reactor system includes three or more fixed bed reactors that can be sequentially rotated from said regeneration mode through a plurality of operating modes and then back to said regeneration mode. When in the operating modes, the reactors are connected in series such that the reactor containing the most recently regenerated (i.e., most active) catalyst contacts the oxygenate-containing feedstock last and the reactor containing the least recently regenerated (i.e., most aged) catalyst contacts the oxygenate-containing feedstock first.

Molecular Sieves

Molecular sieves have been classified by the Structure Commission of the International Zeolite Association according to the rules of the IUPAC Commission on Zeolite Nomenclature. According to this classification, framework-type zeolite and zeolite-type molecular sieves, for which a structure has been established, are assigned a three letter code and are described in the *Atlas of Zeolite Framework Types,* 5th edition, Elsevier, London, England (2001), which is herein fully incorporated by reference.

Crystalline molecular sieves all have a 3-dimensional, four-connected framework structure of corner-sharing [TO$_4$] tetrahedra, where T is any tetrahedrally coordinated cation. Molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition,* Volume 137, pages 1–67, Elsevier Science, B.V., Amsterdam, Netherlands (2001).

Non-limiting examples of molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof, the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of preferred molecular sieves, particularly for converting an oxygenate containing feedstock into olefin(s), include AEL, AFY, AEI, BEA, CHA, EDI, FAU, FER, GIS, LTA, LTL, MER, MFI, MOR, MTT, MWW, TAM and TON. In one preferred embodiment, the molecular sieve used in the present process has an AEI topology or a CHA topology, or a combination thereof, most preferably a CHA topology.

The small, medium and large pore molecular sieves have from a 4-ring to a 12-ring or greater framework-type. In a preferred embodiment, the molecular sieves have 8-, 10- or 12-ring structures and an average pore size in the range of from about 3 Å to 15 Å. In a more preferred embodiment, the molecular sieves, preferably silicoaluminophosphate molecular sieves, have 8-rings and an average pore size less than about 5 Å, such as in the range of from 3 Å to about 5 Å, for example from 3 Å to about 4.5 Å, and particularly from 3.5 Å to about 4.2 Å.

Molecular sieves have a molecular framework of one, preferably two or more corner-sharing [TO$_4$] tetrahedral units, more preferably, two or more [SiO$_4$], [AlO$_4$] and/or [PO$_4$] tetrahedral units, and most preferably [SiO$_4$], [AlO$_4$] and [PO$_4$] tetrahedral units. These silicon, aluminum, and phosphorus based molecular sieves and metal containing derivatives thereof have been described in detail in numerous publications including for example, R. Szostak, *Handbook of Molecular Sieves,* Van Nostrand Reinhold, New York, N.Y. (1992), which is herein fully incorporated by reference.

The more preferred molecular sieves include aluminophosphate (AlPO) molecular sieves and silicoaluminophosphate (SAPO) molecular sieves and substituted, preferably metal substituted, AlPO and SAPO molecular sieves. The most preferred molecular sieves are SAPO molecular sieves, and metal substituted SAPO molecular sieves. In an embodiment, the metal is an alkali metal of Group 1 of the Periodic Table of Elements, an alkaline earth metal of Group 2 of the Periodic Table of Elements, a rare earth metal of Group 3 of the Periodic Table of Elements, including the Lanthanides: lanthanum, cerium, praseodymium, neodymium, samarium, europium, gadolinium, terbium, dysprosium, holmium, erbium, thulium, ytterbium and lutetium; and scandium or yttrium, a transition metal of Groups 4 to 12 of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and has a value from 0 to 1, preferably 0 to 0.5, and most preferably from 0 to 0.3; x, y, and z represent the mole fraction of Al, P and M as tetrahedral oxides, where M is a metal selected from one of Groups 1, 2, 3, 4, 5, 6, 7, 8, 9, 10, 11, 12, 13, 14 and Lanthanide's of the Periodic Table of Elements, preferably M is selected from one of the group consisting of Si, Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18 and AlPO-34 and metal containing derivatives thereof, such as one or a combination of SAPO-18, SAPO-34, AlPO-34 and AlPO-18, and metal containing derivatives thereof, and especially one or a combination of SAPO-34 and AlPO-18, and metal containing derivatives thereof.

In an embodiment, the molecular sieve is an intergrowth material having two or more distinct crystalline phases within one molecular sieve composition. In particular, intergrowth molecular sieves are described in the U.S. Patent Application Publication No. 2002/0165089 and International Publication No. WO 98/15496 published Apr. 16, 1998, both of which are herein fully incorporated by reference. For example, SAPO-18, AlPO-18 and RUW-18 have an AEI framework-type, and SAPO-34 has a CHA framework-type. Thus the molecular sieve used herein may comprise at least one intergrowth phase of AEI and CHA framework-types, especially where the ratio of CHA framework-type to AEI framework-type, as determined by the DIFFaX method disclosed in U.S. Patent Application Publication No. 2002/0165089, is greater than 1:1.

The preferred molecular sieves useful herein for oxygenates to olefins conversion are synthesized by techniques well-known to those skilled in the art, as described in many of the references discussed above.

Metal Oxides

Metal oxides useful herein are those metal oxides, different from typical binders and/or matrix materials, that, when used in combination with a molecular sieve in a catalyst composition, are effective in extending of the useful life of the catalyst composition in the conversion of oxygenates to olefins. Quantification of the extension in catalyst life is determined by the Lifetime Enhancement Index (LEI) as defined by the following equation:

$$LEI = \frac{\text{Lifetime of Catalyst in Combination with Active Metal Oxide}}{\text{Lifetime of Catalyst}}$$

where the lifetime of the catalyst or catalyst composition is the cumulative amount of oxygenate feedstock processed per gram of catalyst composition until the conversion of the oxygenate feedstock by the catalyst composition falls below some defined level, for example 10%. An inactive metal oxide will have little to no effect on the lifetime of the catalyst composition, or will shorten the lifetime of the catalyst composition, and will therefore have a LEI less than or equal to 1. Thus active metal oxides of the invention are those metal oxides, different from typical binders and/or matrix materials, that, when used in combination with a molecular sieve, provide a molecular sieve catalyst composition that has a LEI greater than 1. By definition, a molecular sieve catalyst composition that has not been combined with an active metal oxide will have a LEI equal to 1.0.

In particular, the metal oxides useful herein have an uptake of carbon dioxide at 100° C. of at least 0.03 mg/m$^2$ of the metal oxide, such as at least 0.035 mg/m$^2$ of the metal oxide. Although the upper limit on the carbon dioxide uptake of the metal oxide is not critical, in general the metal oxides useful herein will have a carbon dioxide at 100° C. of less than 10 mg/m$^2$ of the metal oxide, such as less than 5 mg/m$^2$ of the metal oxide. Typically, the metal oxides useful herein have a carbon dioxide uptake of 0.04 to 0.2 mg/m$^2$ of the metal oxide.

In order to determine the carbon dioxide uptake of a metal oxide, the following procedure is adopted. A sample of the metal oxide is dehydrated by heating the sample to about 200° C. to 500° C. in flowing air until a constant weight, the "dry weight", is obtained. The temperature of the sample is then reduced to 100° C. and carbon dioxide is passed over the sample, either continuously or in pulses, again until constant weight is obtained. The increase in weight of the sample in terms of mg/mg of the sample based on the dry weight of the sample is the amount of adsorbed carbon dioxide.

In the Examples reported below, the carbon dioxide adsorption is measured using a Mettler TGA/SDTA 851 thermogravimetric analysis system under ambient pressure. The metal oxide sample is dehydrated in flowing air to about 500° C. for one hour. The temperature of the sample is then reduced in flowing helium to 100° C. After the sample has equilibrated at the desired adsorption temperature in flowing helium, the sample is subjected to 20 separate pulses (about 12 seconds/pulse) of a gaseous mixture comprising 10 weight % carbon dioxide with the remainder being helium. After each pulse of the adsorbing gas the metal oxide sample is flushed with flowing helium for 3 minutes. The increase in weight of the sample in terms of mg/mg adsorbent based on the adsorbent weight after treatment at 500° C. is the amount of adsorbed carbon dioxide. The surface area of the sample is measured in accordance with the method of Brunauer, Emmett, and Teller (BET) published as ASTM D 3663 to provide the carbon dioxide uptake in terms of mg carbon dioxide/m$^2$ of the metal oxide.

Suitable metal oxides include those metal oxides having a Group 4 metal, such as zirconium and/or hafnium, a Group 2 metal, such as magnesium, calcium, strontium and barium and/or a Group 3 metal (including the Lanthanides and Actinides), such as yttrium, scandium, lanthanum, and cerium. In general, oxides of silicon, aluminum, and combinations thereof are not preferred.

It is found that, by including an active metal oxide in combination with a molecular sieve, a catalyst composition can be produced having an LEI in the range of from greater than 1 to 2000, such as from about 1.5 to about 1000. Typically catalyst compositions according to the invention exhibit LEI values greater than 1.1, for example greater than 1.2, and more particularly greater than 1.3, such as greater than 1.5, such as greater than 1.7, such as greater than 2.

In one embodiment, the active metal oxide(s) has a BET surface area of greater than 10 m$^2$/g, such as greater than 10 m$^2$/g to about 300 m$^2$/g. In another embodiment, the active metal oxide(s) has a BET surface area greater than 20 m$^2$/g, such as from 20 m$^2$/g to 250 m$^2$/g. In yet another embodiment, the active metal oxide(s) has a BET surface area greater than 25 m$^2$/g, such as from 25 m$^2$/g to about 200 m$^2$/g. In a preferred embodiment, the active metal oxide(s) includes a yttrium oxide having a BET surface area greater than 20 m$^2$/g, such as greater than 25 m$^2$/g and particularly greater than 30 m$^2$/g.

In one embodiment, it is preferred to utilize a catalyst composition comprising at least two or more metal oxides, preferably selected from oxides of Group 2, Group 3 (including Lanthanide and Actinide series metals) and Group 4 metals. The metal oxides useful in the invention are combinable in many ways to form the active mixed metal oxides. In an embodiment, the metal oxides are mixed together in a slurry or hydrated state or in a substantially dry or dried state. Preferably the metal oxides are contacted in a hydrated state.

In a preferred embodiment, the active mixed metal oxides can be considered as having atomic level mixing of the Group 2, Group 3, and/or Group 4 metals within the oxide, in which the atomic level mixing is achieved during synthesis of the mixed metal oxide.

The active metal oxide(s) used herein can be prepared using a variety of methods. It is preferable that the active metal oxide is made from a metal oxide precursor, preferably a Group 2 metal salt precursor, a Group 3 metal salt precursor, and/or a Group 4 metal salt precursor. Other suitable sources of the metal oxides include compounds that form these metal oxides during calcination, such as oxychlorides and nitrates. Alkoxides are also sources of the metal oxides, for example zirconium n-propoxide.

In one embodiment, the active metal oxide(s) used herein is hydrothermally treated under conditions that include a temperature of at least 80° C., preferably at least 100° C. The hydrothermal treatment typically takes place in a sealed vessel at greater than atmospheric pressure. However, a preferred mode of treatment involves the use of an open vessel under reflux conditions. Agitation of the hydrated metal oxide in a liquid medium, for example, by the action of refluxing liquid and/or stirring, promotes the effective interaction of the hydrated oxide with the liquid medium. The duration of the contact of the hydrated oxide with the liquid medium is conveniently at least 1 hour, such as at least 8 hours. The liquid medium for this treatment typically has a pH of about 6 or greater, such as 8 or greater. Non-limiting examples of suitable liquid media include water, hydroxide solutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$), pyridine and its derivatives, and alkyl/hydroxylamines.

In one embodiment, where the active metal oxide(s) used herein consists of two or more oxides selected from Groups 2, 3, and 4, the active mixed metal oxide may be prepared by impregnation of a precursor to a second oxide onto a preformed oxide. In an alternative embodiment, the first formed oxide may be hydrothermally treated prior to impregnation. For example, a Group 3/Group 4 mixed metal oxide can be prepared by impregnating a hydrothermally treated hydrated oxide of the Group 4 metal with an aqueous solution containing an ion of the Group 3 metal, followed by drying. In a preferred embodiment, the Group 3 metal is lanthanum or yttrium. The resulting material is then calcined, preferably in an oxidizing atmosphere, at a temperature of at least about 400° C., such as at least about 500° C., for example from about 600° C. to about 900° C., and typically from about 650° C. to about 800° C. The calcination time may be up to 48 hours, such as for about 0.5 to about 24 hours, for example for about 1 to about 10 hours. In a practical embodiment, calcination is carried out at about 700° C. for about 1 to about 3 hours.

In yet another embodiment, where the active metal oxide(s) used herein consists of two or more oxides selected from Groups 2, 3, and 4, the active mixed metal oxide may be prepared by combining a first liquid solution comprising a source of at least one of the Group 2, 3, or 4 metals with a second liquid solution comprising a source of an ion of at least one other Group 2, 3, or 4 metal. This combination of two solutions takes place under conditions sufficient to cause co-precipitation of a hydrated precursor to the mixed oxide material as a solid from the liquid medium. Alternatively, the sources of the all the anions of the Group 2, 3, and/or 4 metal oxides may be combined in a single solution. This solution may then be subjected to conditions sufficient to cause co-precipitation of the hydrated precursor to the solid mixed oxide material, such as by the addition of a precipitating reagent to the solution. For example, the precipitating agent(s) preferably is a base such as sodium hydroxide or ammonium hydroxide. Water is a preferred solvent for these solutions.

The temperature at which the liquid medium(s) is maintained during the co-precipitation is typically less than about 200° C., such as in the range of from about 0° C. to about 200° C. A particular range of temperatures for co-precipitation is from about 20° C. to about 100° C. The resulting gel is preferably then hydrothermally treated at temperatures of at least about 80° C., such as at least about 100° C. The hydrothermal treatment typically takes place in a sealed vessel at greater than atmospheric pressure. The gel, in one embodiment, is hydrothermally treated for up to about 10 days, such as up to about 5 days, for example up to about 3 days.

The hydrated precursor to the metal oxide(s) is then recovered, for example by filtration or centrifugation, and washed and dried. The resulting material is preferably then calcined, typically in an oxidizing atmosphere, at a temperature of at least about 400° C., such as at least about 500° C., for example from about 600° C. to about 900° C., and conveniently from about 650° C. to about 800° C., to form the active metal oxide or active mixed metal oxide. The calcination time is typically up to 48 hours, such as for about 0.5 to 24 hours, for example for about 1.0 to 10 hours. In a practical embodiment, calcination is carried out at about 700° C. for about 1 to about 3 hours.

Catalyst Compositions and their Production

Catalyst compositions useful herein include any one of the molecular sieves previously described and one or more of the active metal oxides described above, optionally with a binder and/or matrix material different from the active metal oxide(s). Typically, the weight ratio of the molecular sieve to the active metal oxide(s) in the catalyst composition is in the range of 1:10 to 100:1, such as from 1:5 to 75:1, particularly from 1:1 to 50:1, and more particularly from 2:1 to 40:1.

There are many different binders that are useful in forming the catalyst compositions used herein. Non-limiting examples of binders that are useful alone or in combination include various types of hydrated alumina, silicas, and/or other inorganic oxide sols. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide binder component. For example, an alumina sol will convert to an aluminum oxide binder following heat treatment.

Aluminum chlorhydrol, a hydroxylated aluminum based sol containing a chloride counter ion, has the general formula of $Al_mO_n(OH)_oCl_p.x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7.12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binder is an alumina sol, predominantly comprising aluminum oxide, optionally including some silicon. In yet another embodiment, the binder is peptized alumina made by treating an alumina hydrate, such as pseudobohemite, with an acid, preferably an acid that does not contain a halogen, to prepare a sol or aluminum ion solution. Non-limiting examples of commercially available colloidal alumina sols include Nalco 8676 available from Nalco Chemical Co., Naperville, Ill., and Nyacol AL20DW available from Nyacol Nano Technologies, Inc., Ashland, Mass.

Where the catalyst composition contains a matrix material, this is preferably different from the active metal oxide and any binder. Matrix materials are typically effective in reducing overall catalyst cost, acting as thermal sinks to assist in shielding heat from the catalyst composition for example during regeneration, densifying the catalyst composition, and increasing catalyst strength such as crush strength and attrition resistance.

Non-limiting examples of matrix materials include one or more non-active metal oxides including beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include subbentonites and those kaolins known as, for example, Dixie, McNamee, Georgia and Florida clays. Non-limiting examples of other matrix materials include haloysite, kaolinite, dickite, nacrite, or anauxite. The matrix material, such as a clay, may be subjected to well known modification processes such as calcination and/or acid treatment and/or chemical treatment.

In a preferred embodiment, the matrix material is a clay or a clay-type composition, particularly a clay or clay-type composition having a low iron or titania content, and most preferably the matrix material is kaolin. Kaolin has been found to form a pumpable, high solids content slurry, to have a low fresh surface area, and to pack together easily due to its platelet structure. A preferred average particle size of the matrix material, most preferably kaolin, is from about 0.1 μm to about 0.6 μm with a $D_{90}$ particle size distribution of less than about 1 μm.

Where the catalyst composition contains a binder or matrix material, the catalyst composition typically contains from about 1% to about 80%, such as from about 5% to about 60%, and particularly from about 5% to about 50%, by weight of the molecular sieve based on the total weight of the catalyst composition.

Where the catalyst composition contains a binder and a matrix material, the weight ratio of the binder to the matrix material is typically from 1:15 to 1:5, such as from 1:10 to 1:4, and particularly from 1:6 to 1:5. The amount of binder is typically from about 2% by weight to about 30% by weight, such as from about 5% by weight to about 20% by weight, and particularly from about 7% by weight to about 15% by weight, based on the total weight of the binder, the molecular sieve and matrix material. It has been found that a higher sieve content and lower matrix content increases the molecular sieve catalyst composition performance, whereas a lower sieve content and higher matrix content improves the attrition resistance of the composition.

The catalyst composition typically has a density in the range of from 0.5 g/cc to 5 g/cc, such as from from 0.6 g/cc to 5 g/cc, for example from 0.7 g/cc to 4 g/cc, particularly in the range of from 0.8 g/cc to 3 g/cc.

In making the catalyst composition, the molecular sieve is first formed and is then physically mixed with the active metal oxide(s), preferably in a substantially dry, dried, or calcined state. Most preferably the molecular sieve and active metal oxide(s) are physically mixed in their calcined state. Without being bound by any particular theory, it is believed that intimate mixing of the molecular sieve and one or more active metal oxide(s) improves conversion processes using the molecular sieve composition and catalyst composition of the invention. Intimate mixing can be achieved by any method known in the art, such as mixing with a mixer muller, drum mixer, ribbon/paddle blender, kneader, or the like. Chemical reaction between the molecular sieve and the metal oxide(s) is unnecessary and, in general, is not preferred.

Where the catalyst composition contains a matrix and/or binder, the molecular sieve is conveniently initially formulated into a catalyst precursor with the matrix and/or binder and the active metal oxide is then combined with the formulated precursor. The active metal oxide can be added as unsupported particles or can be added in combination with a support, such as a binder or matrix material. The resultant catalyst composition can then be formed into useful shaped and sized particles by well-known techniques such as spray drying, pelletizing, extrusion, and the like.

Once the molecular sieve catalyst composition is formed in a substantially dry or dried state, to further harden and/or activate the formed catalyst composition, a heat treatment such as calcination, at an elevated temperature is usually performed. Typical calcination temperatures are in the range from about 400° C. to about 1,000° C., such as from about 500° C. to about 800° C., such as from about 550° C. to about 700° C. Typical calcination environments are air (which may include a small amount of water vapor), nitrogen, helium, flue gas (combustion product lean in oxygen), or any combination thereof.

In a preferred embodiment, the catalyst composition is heated in nitrogen at a temperature of from about 600° C. to about 700° C. Heating is carried out for a period of time typically from 30 minutes to 15 hours, such as from 1 hour to about 10 hours, for example from about 1 hour to about 5 hours, and particularly from about 2 hours to about 4 hours.

Oxygenate Conversion Process

The process of the invention is directed to the conversion of a feedstock containing one or more oxygenates to one or more olefin(s). Typically, the feedstock contains one or more aliphatic-containing oxygenate compounds such that the aliphatic moiety contains from 1 to about 50 carbon atoms, such as, from 1 to 20 carbon atoms, for example from 1 to 10 carbon atoms, and particularly from 1 to 4 carbon atoms. Non-limiting examples of suitable oxygenate compounds include alcohols, including straight and branched chain aliphatic alcohols and their unsaturated counterparts, such as methanol, ethanol, n-propanol and isopropanol; alkyl ethers such as dimethyl ether, diethyl ether, methylethyl ether and di-isopropyl ether; alkyl ketones such as dimethyl ketone; aldehydes such as formaldehydes, dimethylcarbonate and various acids such as acetic acid.

In a preferred embodiment of the process of the invention, the feedstock is selected from one or more of methanol, ethanol, dimethyl ether, diethyl ether or a combination thereof, more preferably methanol and dimethyl ether, and most preferably methanol.

The various feedstocks discussed above are converted in the process of the invention primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

Using the catalyst composition of the invention for the conversion of a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 80 weight percent. Moreover, the amount of ethylene and/or propylene produced based on the total weight of hydrocarbon product produced is greater than 40 weight percent, typically greater than 50 weight percent, for example greater than 65 weight percent, and preferably greater than 78 weight percent. Typically, the amount ethylene produced in weight percent based on the total weight of hydrocarbon product produced, is greater than 20 weight percent, such as greater than 30 weight percent, for example greater than 35 weight percent. In addition, the amount of propylene produced in weight percent based on the total weight of hydrocarbon product produced is typically greater than 20 weight percent, such as greater than 25 weight percent, for example greater than 30 weight percent, and preferably greater than 35 weight percent.

In addition to the oxygenate component, such as methanol, the feedstock may contain one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

The present process can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the present process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

The weight hourly space velocity (WHSV), defined as the total weight of feedstock excluding any diluents per hour per weight of molecular sieve in the catalyst composition, typically ranges from about 0.1 $hr^{-1}$ to about 500 $hr^{-1}$, such as from about 1 $hr^{-1}$ to about 100 $hr^{-1}$, for example from about 1 $hr^{-1}$ to about 25 $hr^{-}$.

During the conversion process of the invention, carbonaceous deposits, generally referred to as "coke", are deposited in and/or on the molecular sieve catalysts composition. Although the presence of small amounts of coke may be advantageous in enhancing the ethylene and/or propylene selectivity of the catalyst, the activity of the catalyst decreases rapidly if the coke levels become too high. Accordingly, the catalyst must periodically be regenerated to burn-off some or all of the coke on the catalyst. Regeneration is effected by contacting the coked catalyst composition with a regeneration medium, preferably a gas containing oxygen, under conventional regeneration conditions of temperature and pressure.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172 kPaa) to about 150 psia (1034 kPaa), and conveniently from about 30 psia (207 kPaa) to about 60 psia (414 kPaa).

Coke levels on the catalyst composition can be measured by withdrawing the catalyst composition from the conversion process and determining its carbon content. Typically, the conversion process is allowed to proceed until the coke level on the catalyst composition reaches between about 8 weight percent and about 20 weight percent, such as from about 13 weight percent to about 18 weight percent, based on the weight of the molecular sieve. At this point, the conversion process is suspended and the catalyst is regenerated. Typical levels of coke on the molecular sieve catalyst composition, after regeneration, are in the range of from 0.02 weight percent to about 2.0 weight percent, such as from about 0.02 weight percent to about 0.5 weight percent, based on the weight of the molecular sieve.

Fixed Bed Reactor System

The oxygenate conversion process of the invention is conducted in a fixed bed swing reactor system including a plurality of reactors each containing the catalyst composition described above. In this way, each reactor can be sequentially rotated between an operating mode, wherein the catalyst composition in the reactor is being contacted with the oxygenate-containing feedstock to produce olefin product, and a regeneration mode, wherein the catalyst composition is being contacted with a regeneration medium.

In one simple embodiment, the reactor system can comprise two reactors, a main reactor A and a swing reactor S. In such an embodiment, when the swing reactor S is in its operating mode, the reactor A displaced by the swing reactor is in its regeneration mode for coke removal. After coke has been removed from reactor A, it is returned to the operating mode and the swing reactor S is returned to the regeneration mode for coke removal.

Since freshly regenerated catalyst tends to result in lower ethylene and propylene selectivities than partially coked catalyst, it may be preferable to return the reactor with the regenerated catalyst (coke has been burned off) to a position in the reactor system such that the regenerated catalyst does not contact the fresh feed. One simple method to achieve this is to use three reactors (A, B and C) in series in the reaction circuit and a swing reactor S in the regeneration circuit. The position of A, B and C could be fixed and the swing reactor S arranged to move to the same position as the reactor it replaces in the reaction circuit. A suitable configuration of valving and piping could then be used to alter the direction of flow of the reaction stream through the reactors to ensure that the regenerated catalyst does not contact the fresh feed. For example, when the A reactor is being put into the regeneration circuit for subsequent regeneration, the swing reactor S reactor with freshly regenerated catalyst could replace reactor A in the reaction circuit. Before the displacement of the reactor A by the swing reactor S the reaction stream flow direction might be A→B→C. After the reactor S displaces the reactor A, the reaction stream flow direction could be switched to C→B→S, i.e., the reaction stream enters the reactor series from the C reactor and exits the reactor series through the S reactor. Heat exchanging capability could be added to the reactors so that the exothermic heat of the reaction is removed from each reactor for controlling reactor temperatures. Alternatively, the effluent from each reactor could be passed through a heat exchanger before it is introduced to the next reactor in the reactor series.

Operations of swing reactor systems are described in detail in U.S. Pat. Nos. 4,456,779 and 4,789,528, the entire contents of which are incorporated herein by reference.

The invention will now be more particularly described with reference to the following Examples and the accompanying drawings.

EXAMPLE 1

Five hundred grams of $ZrOCl_2.8H_2O$ and 84 grams of $La(NO_3)_3.6H_2O$ were dissolved with stirring in 3.0 liters of distilled water. Another solution containing 260 grams of concentrated $NH_4OH$ and 3.0 liters of distilled water was prepared. Both solutions were heated to 60° C. and then combined at the rate of 50 ml/min using nozzle mixing to form the final mixture, a slurry. The pH of the final mixture was adjusted to approximately 9 by the addition of concentrated ammonium hydroxide. This slurry was then put in a polypropylene bottle and placed in a steam box (100° C.) for 72 hours. The resulting product formed was recovered by filtration, washed with excess water, and dried overnight at 85° C. A portion of this product, was calcined to 700° C. in flowing air for 3 hours to produce an active mixed metal oxide containing a nominal 10 weight percent La (lanthanum) based on the final weight of the mixed metal oxide and having an uptake of carbon dioxide at 100° C. of 0.085 mg/m$^2$ of the mixed metal oxide.

EXAMPLE 2

The following three catalyst compositions were prepared by mixing SAPO-34 with varying quantities of the mixed metal oxide of Example 1:

(a) 30 mg of SAPO-34/20 mg of mixed metal oxide;

(a) 40 mg of SAPO-34/10 mg of mixed metal oxide; and (a) 50 mg of SAPO-34 alone.

The resultant catalysts were tested in a fixed bed reactor in the conversion of methanol at a temperature of 475° C., a pressure of 25 psig (172.4 kPag) and a methanol weight hourly space velocity (WHSV) of 100 hr$^{-1}$. The results are shown in FIG. 1 from which it will be seen that the catalysts containing the mixed metal oxide of Example 1 aged significantly more slowly than the SAPO-34 alone.

Based on the 100 w/w/hr space velocity data of FIG. 1, it is expected that at a reasonable methanol WHSV of 3 hr$^{-1}$ the methanol conversion would start at >99 wt % and it would take more than 24 hours for the conversion to drop to 50 wt %. During this period of catalyst deactivation, a gradual increase in reactor temperature could maintain the conversion at >90–95 wt %. With a catalyst life greater than 24 hours, fixed bed reactor operating in a swing reactor regeneration (SRR) mode would be economically feasible.

EXAMPLE 3

Fifty grams of $Y(NO_3)_3.6H_2O$ were dissolved with stirring in 500 ml of distilled water. The pH was adjusted to 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of the dried product was calcined to 600° C. in flowing air for 3 hours to produce yttrium oxide ($Y_2O_3$) having an uptake of carbon dioxide at 100° C. of 0.25 mg/m$^2$ of the mixed metal oxide.

EXAMPLE 4

Figure 2:
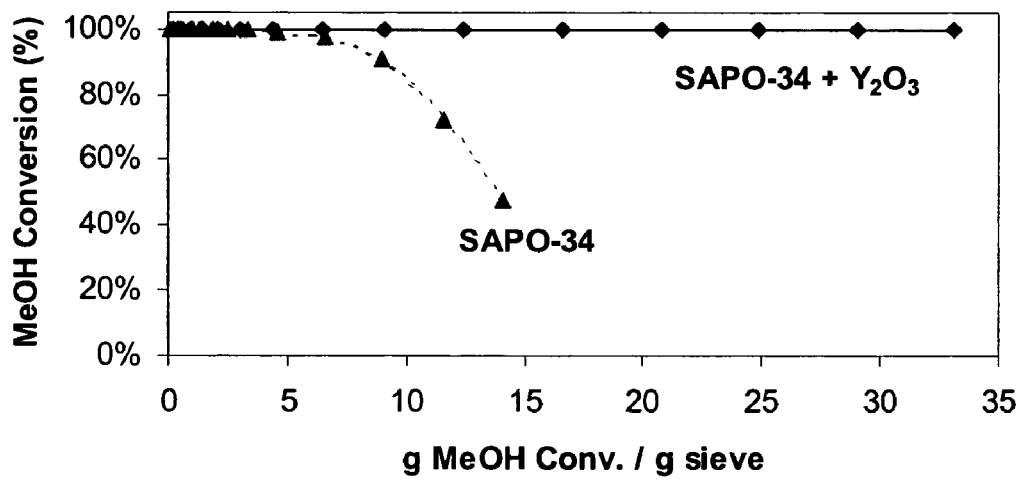
FIG. 2 is a graph illustrating the extended lifetime for methanol conversion for a catalyst composition comprising SAPO-34 molecular sieve and yttrium oxide.

A catalyst composition comprising 40 mg of a SAPO-34 molecular sieve and 10 mg of the yttrium oxide of Example 3 was tested in a fixed bed reactor for the conversion of methanol at a temperature of 475° C., a pressure of 25 psig (172.4 kpag) and a methanol weight hourly space velocity of 50 hr$^{-1}$. The results are shown in FIG. 2 from which it will be seen that the catalyst containing the metal oxide of Example 3 aged significantly more slowly than the SAPO-34 alone. The presence of the metal oxide extends the life of the catalyst sufficiently to enable oxygenate conversion to occur with a fixed bed reactor operating in a swing reactor regeneration (SRR) mode in an economically feasible manner.

While the present invention has been described and illustrated by reference to particular embodiments, those of ordinary skill in the art will appreciate that the invention lends itself to variations not necessarily illustrated herein. For this reason, reference should be made solely to the appended claims for purposes of determining the true scope of the present invention.

We claim:

1. A process for converting an oxygenate-containing feedstock into one or more olefins in a reactor system including a plurality of fixed bed reactors each containing a catalyst composition comprising a molecular sieve and at least one metal oxide, selected from Group 3 metals, Lanthanide series metals, and Group 4 metals of the Periodic Table of Elements, having an uptake of carbon dioxide at 100° C. of at least 0.03 mg/m$^2$ of the metal oxide, wherein each reactor is sequentially rotated between at least one operating mode, wherein the catalyst composition in the reactor is contacted with the oxygenate-containing feedstock, and a regeneration mode, wherein the catalyst composition in the reactor is contacted with a regeneration medium.

2. The process of claim 1 wherein said metal oxide has an uptake of carbon dioxide at 100° C. of at least 0.035 mg/m$^2$ of the metal oxide.

3. The process of claim 1 wherein said metal oxide has an uptake of carbon dioxide at 100° C. of about 0.04 to about 5 mg/m$^2$ of the metal oxide.

4. The process of claim 1 wherein said metal oxide has a surface area greater than 10 m$^2$/g.

5. The process of claim 1 wherein said catalyst composition also includes at least one of a binder and a matrix material different from said metal oxide.

6. The process of claim 1 wherein said catalyst composition also includes a binder and a matrix material each being different from one another and from said metal oxide.

7. The process of claim 6 wherein the binder is an alumina sol and the matrix material is a clay.

8. The process of claim 1 wherein said metal oxide is selected from zirconium oxide, lanthanum oxide, yttrium oxide, scandium oxide, cerium oxide, and mixtures thereof.

9. The process of claim 1 wherein the weight ratio of the molecular sieve to metal oxide is in the range of from 1:10 to 100:1.

10. The process of claim 1 wherein the molecular sieve has a pore diameter less than 6 Angstrom.

11. The process of claim 1 wherein the molecular sieve comprises a framework including at least two tetrahedral units selected from [SiO$_4$], [AlO$_4$] and [PO$_4$] units.

12. The process of claim 11 wherein the molecular sieve comprises a silicoaluminophosphate.

13. The process of claim 11 wherein the molecular sieve comprises a CHA framework-type molecular sieve.

14. The process of claim 11 wherein the molecular sieve further comprises an AEI framework-type molecular sieve.

15. The process of claim 1 wherein each reactor is maintained in said at least one operating mode until the coke level on the catalyst composition reaches between about 8 weight percent and about 20 weight percent, based on the weight of the molecular sieve.

16. The process of claim 1 wherein each reactor is maintained in said at least one operating mode until the coke level on the catalyst composition reaches between about 13 weight percent and about 18 weight percent, based on the weight of the molecular sieve.

17. The process of claim 1 wherein each reactor is maintained in said regeneration mode until the coke level on the catalyst composition decreases to between about 0.02 weight percent and about 2.0 weight percent, based on the weight of the molecular sieve.

18. The process of claim 1 wherein each reactor is maintained in said regeneration mode until the coke level on the catalyst composition decreases to between about 0.02 weight percent and about 0.5 weight percent, based on the weight of the molecular sieve.

19. The process of claim 1 wherein the reactor system comprises at least three of said fixed bed reactors and each reactor is sequentially rotated from said regeneration mode to a first operating mode, then to at least a second operating mode and then back to said regeneration mode, wherein reactors in said first and second operating modes are connected in series such that the oxygenate-containing feedstock contacts the catalyst composition in a reactor in the second operating mode before contacting the catalyst composition in a reactor in the first operating mode.

20. The process of claim 1 wherein the oxygenate-containing feedstock comprises methanol, ethanol, dimethyl ether, diethyl ether or a combination thereof.

21. The process of claim 1 wherein, in said at least one operating mode, the catalyst composition is contacted with the oxygenate-containing feedstock at a temperature of about 200° C. to about 1000° C. a pressure of about 0.1 kPaa to about 5 Mpaa and a weight hourly space velocity (WHSV) of about 0.1 $hr^{-1}$ to about 500 $hr^{-1}$.

22. The process of claim 1 wherein, in said regeneration mode, the catalyst composition is contacted with the regeneration medium at a temperature of about 200° C. to about 1500° C. and a pressure of about 15 psia (103 kPaa) to about 500 psia (3448 kPaa).

23. A process for converting an oxygenate-containing feedstock into one or more olefins in a reactor system including a plurality of fixed bed reactors each containing a catalyst composition comprising a molecular sieve and at least one metal oxide, selected from Group 3 metals, Lanthanide series metals, Actinide series metals, and Group 4 metals of the Periodic Table of Elements, having an uptake of carbon dioxide at 100° C. of at least 0.03 $mg/m^2$ of the metal oxide, wherein each reactor is sequentially rotated between a plurality of operating modes, wherein the catalyst composition in the reactor is contacted with the oxygenate-containing feedstock to produce said one or more olefins and generate coke on the catalyst composition, and a regeneration mode, wherein the catalyst composition in the reactor is contacted with a regeneration medium, the process comprising connecting said reactors in said operating modes in series such that the feedstock contacts the most heavily-coked catalyst first and contacts the newly regenerated catalyst last.

* * * * *